United States Patent [19]
Aylsworth et al.

[11] Patent Number: 5,495,848
[45] Date of Patent: Mar. 5, 1996

[54] MONITORING SYSTEM FOR DELIVERY OF THERAPEUTIC GAS

[75] Inventors: Alonzo C. Aylsworth, Glencoe; Gregory R. Miller, Chesterfield, both of Mo.

[73] Assignee: Nellcar Puritan Bennett, St. Charles, Mo.

[21] Appl. No.: 344,848

[22] Filed: Nov. 25, 1994

[51] Int. Cl.⁶ .................................................. A61M 16/00
[52] U.S. Cl. .................... 128/207.18; 128/204.23; 128/205.24
[58] Field of Search .................... 128/207.18, 200.14, 128/200.23, 202.22, 202.21, 203.12, 203.15, 203.23, 203.14, 203.25, 204.23, 204.26, 205.24

[56] References Cited

U.S. PATENT DOCUMENTS

| | | | |
|---|---|---|---|
| 4,457,303 | 7/1984 | Durkan | 128/204.24 |
| 4,462,398 | 7/1984 | Durkan et al. | 128/200.14 |
| 4,677,975 | 7/1987 | Edgar et al. | 128/200.14 |
| 4,681,099 | 7/1987 | Sato et al. | 128/204.23 |
| 4,686,975 | 8/1987 | Naimon et al. | 128/204.23 |
| 5,134,995 | 8/1992 | Gruenke et al. | 128/204.23 |
| 5,137,017 | 8/1992 | Salter | 128/207.18 |
| 5,363,842 | 11/1994 | Mishelevich et al. | 128/200.14 |

FOREIGN PATENT DOCUMENTS

| | | | |
|---|---|---|---|
| 87/04354 | 7/1987 | WIPO | 128/200.23 |
| 90/10470 | 9/1990 | WIPO | 128/203.15 |
| 91/06334 | 5/1991 | WIPO | 128/200.23 |

*Primary Examiner*—Christopher A. Bennett
*Assistant Examiner*—Eric P. Raciti
*Attorney, Agent, or Firm*—Paul M. Denk

[57] ABSTRACT

An apparatus for monitoring and controlling the flow of a therapeutic gas to a patient. The apparatus includes a gas source, a flow management module and an electronics module. The flow management module contains a valve assembly and a sensor. The valve assembly contains a first valve to control the inflow of the therapeutic gas. The second valve controls the inflow of ambient air. When the valve assembly is deenergized the first valve is open allowing the flow of gas through the apparatus. The second valve is closed. When the valve assembly is energized, the first valve is closed stopping the flow of gas and the second valve is open allowing the inflow of ambient air. The sensor senses changes in the flow of the gas or ambient air and transmits a signal to the electronics module. The electronics module can be preprogrammed to control the valve assembly, determine respiratory rate, control the flow of therapeutic gas, store or transmit data in response to signals sent by the sensor.

8 Claims, 1 Drawing Sheet

MONITORING SYSTEM FOR DELIVERY OF THERAPEUTIC GAS

BACKGROUND OF THE INVENTION

The is invention relates to an inhalation therapy device, more particularly to a monitoring device for monitoring and controlling the flow of a therapeutic gas.

Generally, a patient with a pulmonary disease, breathing disorder or oxygen deficit is given a prescription that indicates the concentration of oxygen, the flow requirement of oxygen or volume and the usage, for example, the hours per day of oxygen delivery. In some cases, the prescription will include the precise hours of the day the patient is to receive the oxygen therapy. For example, the patient's prescription may call for two liters of oxygen per minute for two hours during the day and eight hours at night. Or, in some cases, the prescription may call for four liters of oxygen per minute for twenty-four hours a day. Usually the prescription is based upon oxygen requirements established in a controlled setting such as during hospitalization. The prescription is continued at home after discharge from the hospital. Delivery of oxygen therapy at home should correspond to the prescription developed in the hospital. Failure to comply with the prescription could be harmful to the patient. Oxygen concentrators have been developed and commercialized to provide the delivery of near pure oxygen to the individual patient to satisfy medical needs.

SUMMARY OF THE INVENTION

It is among the principal objects of the invention to provide a monitoring system for monitoring compliance with an oxygen prescription.

It is another object of the present invention to provide a monitoring system that contains a breathing detector, a control, and a transmitter.

It is yet another object of the invention to provide a monitoring system having the capability to detect, log, store or transmit data concerning the patients breathing patterns and adherence to a prescription.

Still another object of the present invention is to provide a monitoring system that has an inhalation-activated switch for turning on a gas source.

Another object of the present invention is to provide as switch that will automatically shut off the flow of gas when a blockage of flow is detected.

In accordance with the invention, generally stated, a monitoring system for monitoring the delivery of a therapeutic gas such as oxygen to a patient is provided having a gas source, a flow management module, and an electronics module. The flow management module contains a valve and a sensor. The valve is programmed to open to allow flow of gas from the gas source through the system to a patient and to close periodically so that the patient's own breathing can be monitored. When closed, the patient draws ambient air into the valve and across the sensor. The sensor transmits data to the electronics module. The electronics module can be preprogrammed to determine the presence of inhalations, rate of inhalations and strength of inhalations. The data is stored in the electronics module for retrieval and evaluation or transmitted via telephone. The electronics module can be preprogrammed to activate the gas source or shut off the gas source in response to such data.

DESCRIPTION OF THE PREFERRED EMBODIMENT

Figure 1:
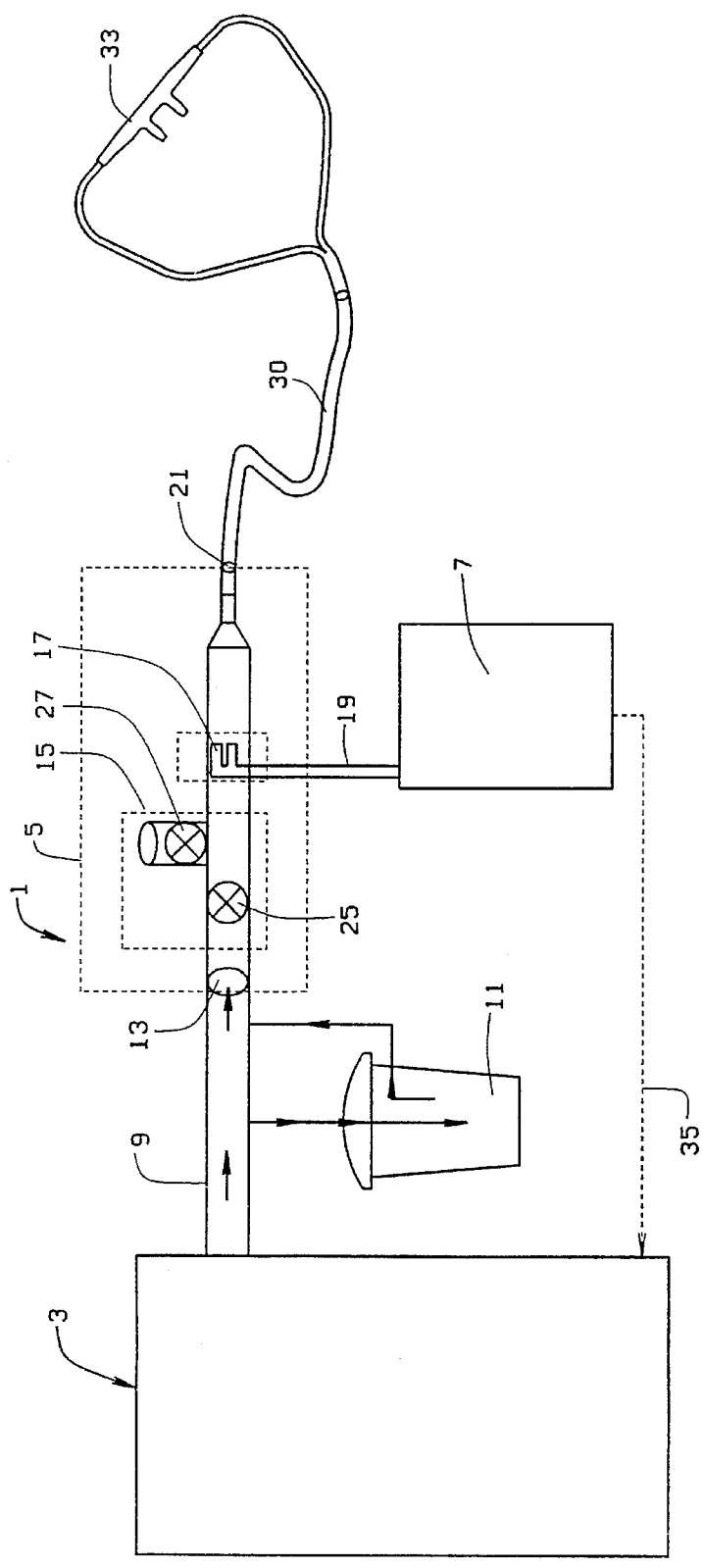
FIG. 1 is a diagrammatic view of the monitoring system of the present invention.

The monitoring system of the present invention is indicated generally by reference numeral 1 in FIG. 1. As illustrated, system I has a gas source 3, a flow management module 5 and an electronics module 7. The individual elements of system I will now be described in detail.

Gas source 3 can be an oxygen generator, a liquid oxygen source, a high pressure cylinder source or any other appropriate therapeutic gas source. Preferably though, an oxygen concentrator supplies the near pure supply of oxygen. A gas tubing 9 is appropriately connected to gas source 3. An optional humidifier 11 can be connected into tubing 9. Tubing 9 is connected to flow management module 5 through port 13. Flow management module 5 contains a 3-way valve assembly 15 and a sensor 17. Sensor 17 is connected to the electronics module 7 by conventional wiring 19. Electronics module 7 is available from Motorola Company of Austin, Tex., Model No. C.S.I.C. MC68HC05 or greater, and is fabricated to provide a determination of patterns of inhillations of the patient. Valve assembly 15 will be described in greater detail below. Sensor 17 can be a flow sensor or a pressure sensor with an associated temperature compensator, depending upon the desired characteristics of the sensor.

Figure 2A:
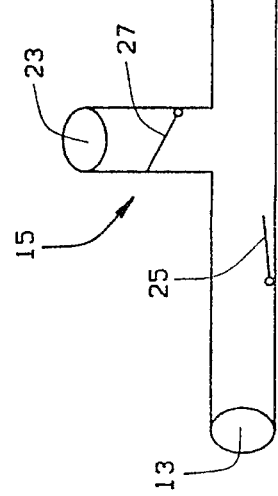
FIG. 2A is a diagrammatic view of the valve assembly of the monitoring system of the present invention in a de-energized state.
Figure 2B:
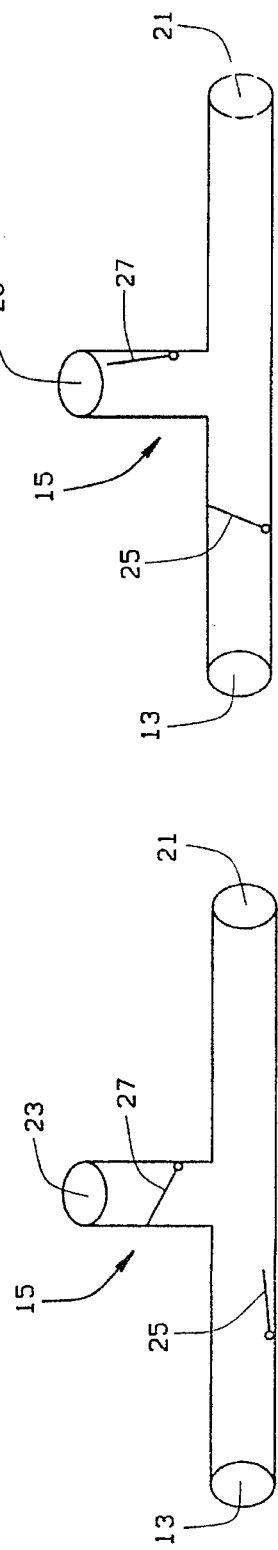
FIG. 2B is a diagrammatic view of the valve assembly of the monitoring system of the present invention in an energized state.

Valve assembly 15 is shown in greater detail in FIGS. 2A and 2B. Valve assembly 15 has gas inlet port 13, a gas outlet port 21, and an ambient air entry port 23. There is a first or gas inlet control valve 25 adjacent the gas inlet port. There is a second or an ambient air control valve 27 adjacent the ambient air entry port. FIG. 2A shows valve assembly 15 in a de-energized state. Valve 25 is open and valve 27 is closed. FIG. 2B shows valve assembly 15 in an energized state wherein valve 25 is closed and valve 27 is open. The functions of the respective valves will be described in greater detail hereinafter.

A tubing 30 is connected to the flow management module 5 at a port 21. Tubing 30 is conventional and is operatively connected to a nasal cannulae 33. It will be appreciated by those skilled in the art that nasal cannulae 33 is designed to provide access to the gas flowing through the system by a patient. Therefore, cannulae 33 could be replaced with a mask, endotracheal tube or other appropriate access means without departing from the scope of the invention.

Monitoring system 1 functions to detect a patient's breathing patterns or complaince with a respiratory presecription as follows: a patient ( not shown) receives oxygen or other therapeutic gas from gas source 3 through nasal cannulae 33 according to a physician's prescription. Valve assembly 15 is in the de-energized state (FIG. 2A) to allow flow of gas through the system. Periodically, valve assembly 15 is energized. The valve assembly is energized by the electronics module 7, which is conventionally programmed to perform a multitude of functions which will be described hereinafter. For example, the valve assembly is energized every 15 minutes. The respective valves 25 and 27 are positioned as shown in FIG. 2B. Valve 25 is closed and valve 27 is open. The flow of gas from the gas source is blocked by valve 25 and does not contact sensor 17. Valve 27 opens and allows ambient air to flow into the system through port 23. The ambient air contacts sensor 17 and flows through tubing 30 and cannulae 33 to the patient. When the ambient air contacts sensor 17, the sensor sends a voltage signal, via wires 19, to electronics module 7. The signal is processed by the electronics module. As will be appreciated, a significant amount of ambient air will flow into the system through port 23 only if the patient is breathing. The air is drawn into the system by the patient's inhalations. Adequate air flow over sensor 17 is required for accurate and precise measurements of the patient's inhalations. Since valve 25 is closed back pressure is minimized thus allowing maximum flow through open valve 27 and across sensor 17. Upon detection of the inhalation, the electronics module will de-energize valve assembly 15 to allow flow of the gas. Should sensor 17 not detect a flow of ambient air during a preset period of time that valve assembly 15 is energized, valve assembly 15 is de-energized to allow unrestricted flow of the gas to the patient. For example, the system can be programmed to de-energize the valve assembly if sensor 17 does not detect a flow of ambient air within 10 seconds of being energized. If the patient fails to inhale or does inhale during the predetermined time period, electronics module 7 logs that data in a memory for recall. The electronics module can be connected to a separate clock or to a telephone so that the record of inhalations, i.e. breathing patterns and respiratory rate, can be transmitted to a health care professional. Furthermore, the system can be connected to an alarm or other alerting means. The electronics module can contain an analog storage device or a standard microprocessor (Motorola). By detecting inhalations and non-inhalations, monitoring system 1 can track noncompliance and compliance with a prescription, log patient problems, and detect equipment malfunctions.

Monitoring system 1 can be used to switch on gas source 3 in response to the patient's inhalations. For example, gas source 3 can be an oxygen concentrator. Valve 15 is in an energized state and the patient is breathing ambient air. Electronics module 7 is preprogrammed to respond to inhalations transmitted by sensor 17. First, electronics module 7 may be programmed to activate the oxygen concentration upon the detection of an inhalation or pattern of inhalations. This would be advantageous if the patient is not positioned near the oxygen generator or is too debilitated to manually activate the gas source. If the patient requires oxygen, he or she can employ cannulae 33 or other mechanical device, and use a predetermined pattern oil inhalations, or exhalations, or flow pulses generated by a mechanical device to activate the 02 generator. For example, the pattern could be a predetermined pattern of three 1 second inhalations over a 6 second period. The flow management module 5 detects the pattern and transmits it to the electronics module 7 via circuitry 35. The pattern is recognized and a signal is sent from the electronics module to the oxygen concentrator to switch it on. Monitoring system 1 is thus programmed to differentiate the patient's inhalation pattern from a false pattern. On occasion tubing 30, for example, may be moved or repositioned causing movement of air across sensor 17. Such air movement potentially could give a false signal. Since a predetermined pattern of inhalations is required to activated the oxygen generator, false starting of the gas source is prevented.

Monitoring system 1 can be preprogrammed to allow the patient to switch off gas flow by the intentional blocking the flow of gas through cannulae 33 with a predetermine blocking pattern similar to the pattern required to activate the gas source, as just described. A stop-cock or other easily manipulated valve means (not shown) can be installed in cannulae 33 or tube 30. The patient can manipulate the stop-cock or valve in a predetermined pattern that will interrupt gas flow across sensor 17. This pattern will be transmitted to electronics module 7 for processing. The tubing 9 in which the sensor 17 locates may have a series of orifices (not shown), which provides for regulation of the amount of oxygen passing through for sensing and detecting to furnish more accurate readouts from the module 7. When the proper pattern is detected, a signal is sent to gas source 3 via circuitry 35 and the gas source is switched off. Since a predetermined pattern is required, false shut-offs are avoided. The sensor may be obtained from Microswitch Co., Division of Honeywell, of Freeport, Ill., Model No. AWM-3300V.

It is possible to send the gas from gas source 3 in pulses through the system to alert the patient of the proper flow of gas. For example, if two liters of oxygen are sent through the system and detected by sensor 17, the electronics module can be programmed to send a signal to gas source 3 via circuitry 35 to provide two pulses of gas through the system to the patient. There is a break in the pulses and then another series of pulses sent. The predetermined series of pulses tell the patient that the appropriate number of liters of oxygen have been sent. Furthermore, the malfunction alarm system on an oxygen concentrator, for example, could be programmed to send a series of gas pulses through the system to the patient in the event of malfunction. It also is possible to have the electronics module provide audio signals indicating flow rate. A predetermine audio signal can indicate the amount of gas delivered. For example, two beeps periodically sounded would indicate the delivery of two liters of gas.

Monitoring system 1 can be designed to give a continuous read-out of gas flow through the system. Sensor 17 can be a pressure transducer with a predetermined orifice or restriction device to measure flow through the sensor. Sensor 17 is connected to the electronics module 7 which, in turn, generates a log of the flow rate, volume and so on. Furthermore, electronics module 7 can be programmed to activate an alarm if there is an interruption of a predetermined flow rate.

The monitoring system of the present invention also can be used to conserve gas from gas source 3. The gas can be controlled by the patient's inhalations. For example, sensor 17 can be constructed to sense inhalations of the gas from the gas source by sensing an increased flow rate through the system or other appropriate means. The increased flow rate would indicate an inhalation. A signal is sent from sensor 17 to electronics module 7 to de-energize valve assembly 15. Valve assembly 15, in the energized state, allows gas from the gas source to flow to the patient. When the patient stops inhaling, the flow rate decreases and a signal is sent to electronic module to energize valve assembly 15. In the energized state valve 25 is closed and valve 27 is open, as previously described. The flow of gas is stopped thereby conserving gas. As soon as the patient inhales, an increased flow of ambient air through valve 27 and across sensor 17 elicits a signal to de-energized valve assembly 15 to allow the flow of gas through the system. When valve assembly 15 is in an energized mode and gas is being conserved, electronics module 7 can send a signal to the gas source, for example an oxygen concentrator, to switch the concentrator into a conventional gas conservation mode. The concentrator then adjusts for maximum efficiency. If, for example, the oxygen concentrator is equipped with a multiple or variable speed compressor motor, the concentrator may receive a signal to operate at a lower speed and still provide the appropriate amount of oxygen.

The monitor system of the present invention can be programmed to employ a safety shut-off system. If the sensor detects no inhalations for a predetermined period of time, the electronics module shuts off the source of gas. This prevents oxygen saturation of bedding, sofas, or furniture that can be a fire hazard.

It will be appreciated that various changes and modifications can be made in the monitoring system of the present invention without departing from the scope of the appended claims. Therefore, the foregoing description and drawings are intended to be illustrative only and should not be viewed in a limiting sense.

We claim:

1. A monitoring system for periodically detecting the flow of a therapeutic gas from a gas source to a patient, comprising:

a gas source for providing a therapeutic gas;

a flow management module operatively connected to the gas source, said flow management module containing a valve assembly and a sensor;

an electronics module operatively connected to the sensor;

means for delivering the therapeutic gas no a patient;

said valve assembly further comprising a first valve positioned between the gas source, the sensor, and the breathing patient, and a second valve positioned between an ambient airport, the sensor, and the breathing patient, said valve assembly having an energized state wherein said first valve is in an open position and said second valve is in a closed position;

the sensor having means for detecting a flow of the therapeutic gas or a flow of ambient air through the valve assembly and independently to the breathing patient;

the sensor further comprising means for sending a signal to the electronics module in response to the flow of the therapeutic gas or the flow of ambient air;

said electronics module logs, displays, and/or transmits the flow of the therapeutic gas or the flow of ambient air through the valve assembly;

said electronics module further having means for determining a presence, rate and strength of inhalations based upon the flow of ambient air through the valve assembly and to the breathing patient, when the valve assembly is in said energized state;

said electronics module further having means for activating or deactivating said gas source in response to its determination of the rate of inhalations of the patient of ambient air;

said electronic modules further comprising means for activating or deactivating the gas source in response to a predetermined pattern of inhalations or a predetermined pattern of interruptions in a flow of the ambient air through the valve assembly and to the breathing patient; and wherein said predetermined pattern of inhalations and predetermined pattern of interruptions in the flow of ambient air prevent an improper activation of the gas source or an improper deactivation of the gas source.

2. The monitoring system of claim 1 further comprising means for conserving a flow of gas from the gas source controlled by inhalations of the gas by the user.

3. The monitoring system of claim 2 wherein the means for conserving the flow of gas further comprising the sensor disposed to send a signal to the electronics module between inhalations by a user, the electronics module disposed to send a signal to the gas source to stop the flow of gas thereby conserving the flow of gas between inhalations.

4. The monitoring system of claim 1 further comprising means for detecting and transmitting a respiratory rate of a patient using the system.

5. An apparatus for monitoring and controlling the flow of gas to a patient comprising:

a gas source;

a flow management module operatively connected to the gas source, the flow management module containing a valve assembly and a sensor;

said valve assembly having a first valve for controlling the inflow of the gas, and a second valve for controlling the inflow of ambient air;

said valve assembly having a de-energized state wherein said first valve is opened allowing the inflow of gas and said second valve is closed, and an energized state wherein said first valve is closed blocking the inflow of the gas and said second valve is opened allowing the inflow of ambient air;

said sensor disposed to sense a change in flow of gas or ambient air through said valve assembly and transmitting a signal in response to said change;

a programmable electronics module operatively connected to said valve assembly and having means for energizing or de-energizing said valve assembly, said electronics module being responsive to said signal transmitted by said sensor to energize or de-energize said valve assembly;

said electronics module further comprising means for controlling said gas source;

said electronic module further comprising means for storing and transmitting data;

said electronics module further comprising means for activating said gas source in response to a predetermined pattern of inhalations of ambient air by the breathing patient as determined by said sensor;

said electronic module further comprises means for deactivating said gas source in response to a predetermined pattern of interruptions in a flow of gas through the apparatus; and whereby the electronic module is preprogrammed to determine the presence of inhalations, rate of inhalations, and strength of inhalations, due to the patient's breathing in of ambient air when said valve assembly is in an energized state.

6. The apparatus of claim 5 further comprising means for indicating to a user a status of a flow of gas through the apparatus.

7. The apparatus of claim 6 wherein said means for indicating to a user the status of the flow of gas further includes means for creating a pattern of pulses of the gas through the apparatus.

8. The apparatus of claim 6 wherein said means for indicating to a user the status of the flow of gas further includes means for creating an audible signal indicating the status of the flow of gas through the apparatus.

* * * * *

UNITED STATES PATENT AND TRADEMARK OFFICE
CERTIFICATE OF CORRECTION

PATENT NO. : 5,495,848

DATED : March 5, 1996

INVENTOR(S) : Alonzo C. Aylsworth, et al.

It is certified that error appears in the above-identified patent and that said Letters Patent is hereby corrected as shown below:

Please change name of Assignee from "Nellcar" to ---Nellcor---.

Column 5, claim 1, line 30, "no" to ---to---.

Signed and Sealed this

Eighteenth Day of June, 1996

Attest:

BRUCE LEHMAN

Attesting Officer

Commissioner of Patents and Trademarks